(12) United States Patent
Li et al.

(10) Patent No.: US 11,549,949 B2
(45) Date of Patent: Jan. 10, 2023

(54) METHOD FOR EVALUATING IN VIVO PROTEIN NUTRITION BASED ON LC-MS-MS TECHNIQUE

(71) Applicant: Nanjing Agricultural University, Jiangsu (CN)

(72) Inventors: Chunbao Li, Jiangsu (CN); Guanghong Zhou, Jiangsu (CN); Chao Wang, Jiangsu (CN); Xinglian Xu, Jiangsu (CN)

(73) Assignee: NANJING AGRICULTURAL UNIVERSITY, Nanjing (CN)

( * ) Notice: Subject to any disclaimer, the term of this patent is extended or adjusted under 35 U.S.C. 154(b) by 337 days.

(21) Appl. No.: 16/623,692

(22) PCT Filed: May 3, 2018

(86) PCT No.: PCT/CN2018/085446
§ 371 (c)(1),
(2) Date: Dec. 17, 2019

(87) PCT Pub. No.: WO2019/037465
PCT Pub. Date: Feb. 28, 2019

(65) Prior Publication Data
US 2020/0141946 A1 May 7, 2020

(30) Foreign Application Priority Data

Aug. 25, 2017 (CN) .......................... 201710742758.6

(51) Int. Cl.
*G01N 33/68* (2006.01)
*G16B 20/00* (2019.01)
(Continued)

(52) U.S. Cl.
CPC .......... *G01N 33/6848* (2013.01); *C07K 1/16* (2013.01); *G01N 1/28* (2013.01); *G01N 30/06* (2013.01);
(Continued)

(58) Field of Classification Search
None
See application file for complete search history.

(56) References Cited

U.S. PATENT DOCUMENTS

2016/0033511 A1\* 2/2016 Pannell ............ G01N 33/57438
435/6.12

FOREIGN PATENT DOCUMENTS

CN 106442683 A 2/2017

OTHER PUBLICATIONS

Yu, Yang, et al. Protein digestomic analysis reveals the bioactivity of deer antler velvet in simulated gastrointestinal digestion, Food Research International, vol. 96, pp. 182-190 (Year: 2017).\*
(Continued)

*Primary Examiner* — Xiaoyun R Xu
(74) *Attorney, Agent, or Firm* — Gary J. Gershik (57) ABSTRACT

Disclosed is a method for evaluating in vivo protein nutrition based on an LC-MS-MS technique, including the following steps: (1) collecting contents from different intestinal segments, and extracting and isolating protein ingredients; (2) determining the concentration of proteins; (3) treating before carrying out mass spectrometry: including digestion and desalting of a whole protein solution; (4) LC-MS-MS analysis; (5) database searching; and (6) data processing. Proteomic technology is used to identify proteins in the contents of different intestinal segments and digestive products thereof, and the source of the proteins in the contents of different intestinal segments and the contents thereof can be determined therefrom. Through bioinformatic analysis, the
(Continued)

EXHIBIT B function of differential proteins in the body can be further understood, where the gene expression of enzymes related to protein digestion and metabolism may be different, thereby providing a scientific basis for further scientific evaluation of protein digestion and utilization.

8 Claims, 3 Drawing Sheets

(51) Int. Cl.
    C07K 1/16      (2006.01)
    G01N 1/28      (2006.01)
    G01N 30/06     (2006.01)
(52) U.S. Cl.
    CPC ......... *G01N 33/6818* (2013.01); *G16B 20/00* (2019.02); *G01N 2800/02* (2013.01); *G01N 2800/06* (2013.01)

(56) References Cited

OTHER PUBLICATIONS

Sauer, W.C. et al., "A Modified Nylon Bag Technique for Determining Apparent Digestibilities of Protein in Feedstuffs for Pigs", Can. J. Anim. Sci., vol. 63, 1983, pp. 233-237.
Sun, M. and Mu, T., "Development of methods for the determination of protein digestibility", Science and Technology of Food Industry, vol. 32, 2011, pp. 382-385 (with English abstract).
Yu, Y. and Jin, Y., "Food protein digestomics study by liquid chromatograph-tandem mass spectrometry", Abstracts of the 13th Annual Meeting of CIFST, 2016, pp. 82-83 (with English abstract).
Yuan, K. et al., "Advances in Research on Small Intestine Digestion of Ruminant Proteins", Chinese Journal of Animal Husbandry and Veterinary Medicine, No. 4, 2008, pp. 4-5.
International Search Report issued by the International Searching Authority (ISA/O.E.P.M.) dated Aug. 3, 2018 in connection with International Application No. PCT/CN2018/085446.

* cited by examiner

EXHIBIT B

METHOD FOR EVALUATING IN VIVO PROTEIN NUTRITION BASED ON LC-MS-MS TECHNIQUE

BACKGROUND

Technical Field

The present invention belongs to the technical field of proteomics and relates to a method for evaluating in vivo protein nutrition based on an LC-MS-MS technique.

Related Art

At present, a relatively authoritative method for measuring the in vivo protein digestibility is the fecal nitrogen balance experiment. The principle is that dietary proteins enter the gastrointestinal tract through the esophagus, pepsin in the stomach digests the dietary proteins. Polypeptides enter the small intestine (duodenum, jejunum and ileum) and are digested by trypsin and chymotrypsin, and finally, a small amount of microbial cells, fecal metabolic nitrogen shedding from the intestinal mucosa. Proteins that are not completely digested or absorbed pass through the colon and are excreted in the form of feces. The proportion of a difference between the intake nitrogen and fecal nitrogen accounting for the intake nitrogen is the apparent digestibility. Although 5% of high-digestive casein will be added and then the metabolic fecal nitrogen is measured to correct the apparent digestibility so as to obtain true digestibility, this method does not truly reflect the digestion and absorption of proteins in the body. The method for measuring the in vivo digestibility is complicated in operation and long in time, and the experimental animals have higher requirements on the external environment. The traditional method only pays attention to nitrogen intake and nitrogen excretion, lacks in-depth understanding of the digestion, absorption and metabolism in the body, and cannot truly reflect protein digestion in the body. Therefore, it is necessary to establish a new method that can truly evaluate the in vivo digestion of dietary proteins.

Proteomics is a discipline that studies the proteome using techniques such as protein isolation, identification and quantification. Mass spectrometry-based proteomics technology is especially widely used in the field of life sciences. Mass spectrometry is the core technology in proteomics research, is the basic means for protein identification, and can accurately measure the relative molecular mass, amino acid sequence and post-translational modification of peptides and proteins. At present, liquid chromatography-mass spectrometry has become the mainstream method for high-throughput analysis of proteins. Usually, LC and MS are tandem, and the peptides separated by the LC are ionized and charged by an external electric field before entering the MS. The ionized peptide enters the primary MS for determining the precise molecular mass of the peptide, the number of charges, the abundance of the peptide (i.e., the signal intensity on the mass spectrum), and then enters the secondary mass spectrometer for inferring the amino acid composition and order of the peptides by Mascot database search and sequence alignment. The databases are compared by the Maxquant software and the protein databases of three sources (host, diet, and microorganisms) are compared to collect all the information on digestion, absorption and conversion of proteins in vivo.

SUMMARY

The present invention provides a method for evaluating in vivo protein nutrition based on an LC-MS-MS technique.

The objective of the present invention can be achieved by the following technical solutions:

A method for evaluating in vivo protein nutrition based on an LC-MS-MS technique, includes the following steps:

(1) collecting contents from different intestinal segments, and extracting and isolating protein ingredients;

(2) determining the concentration of proteins;

(3) treating before carrying out mass spectrometry: including digesting and desalting of a whole protein solution;

(4) LC-MS-MS analysis: a peptide product is obtained by carrying out reversed phase liquid chromatography using a nanoliter liquid chromatograph mass spectrometer on a digested, desalted and blow-dried sample, and analysis is performed by a nanoliter ion source by tandem mass spectrometry using an LTQ-Orbitrap mass spectrometer;

(5) database searching: MaxQuant_1.5.8.3 software is used to search for 30 individual original spectral files running on shotgun LC-MS/MS, respectively;

(6) data processing: databases are searched from three aspects for proteins in the contents of each intestinal segment, where the specific search sources are the protein databases of dietary proteins, host and intestinal microorganisms. By analyzing the protein data from three sources, the following information can be achieved: (i) the digestion of dietary proteins across the whole intestine, and the type and abundance of the identified proteins or peptides; (ii) the type and functions of proteins secreted by the host under the induction of the dietary proteins; and (iii) the composition of intestinal microorganisms responding to the dietary proteins and their crosstalk with the host.

The different intestinal segments are preferably duodenum, jejunum, cecum and/or colon.

Preferably, in the evaluation method consistent with the present invention, the protein concentration in the contents from different intestinal segments is measured using a BCA kit.

Preferably, in the evaluation method consistent with the present invention, the digesting of the whole protein solution includes the following steps:

(1) activating a 10KD ultrafiltration tube with ultrapure water;

(2) taking 200 μg of protein, calculating a volume for 200 μg of protein as X ml, then supplementing Y ml of 8M urea and 50mMTris-HCl (pH8.0) to a 200 μl system (i.e. X+Y=200 μl) into the ultrafiltration tube, and performing centrifugation at 14000×g for 15 min;

(3) adding 200 μl of 8M urea and 50mMTris-HCl (pH8.0), performing centrifugation at 14000×g for 15 min;

(4) adding 200 μl of 8M urea and 50mMTris-HCl (pH 8.0), 5 μl of 1M DTT to the solution, heating at 60° C. for 60 min, cooling to room temperature, and performing centrifugation at 14000×g for 15 min;

(5) adding 200 μl of 8M urea and 50mMTris-HCl (pH 8.0), 20 μl of 0.5M IAM, incubating at room temperature in the dark for 45 min, and performing centrifugation at 14000×g for 15 min;

(6) adding 200 μl of 50 mM, $NH_4HCO_3$ (pH 7.8), performing centrifugation at 14000×g for 15 min, repeating once;

(7) renewing an ultrafiltration tube bottom tube, adding 200 μl of 50 mM $NH_4HCO_3$ (pH 7.8), and according to the ratio of Trypsin to substrate protein at 1:50, adding an enzyme solution (i.e., adding 40 μl), and incubating at 37° C. for 16 h (overnight);

(8) after incubation, performing centrifugation at 14000×g for 25 min, supplementing 50 μl of 50 mM NH$_4$HCO$_3$ (pH 7.8), performing centrifugation at 14000×g for 25 min, where the contents in the bottom tube are the peptides after enzymatic hydrolysis, and adding formic acid to the solution to a final concentration of 0.2%; and (9) transferring a sample into a 1.5 ml centrifuge tube and performing blow-drying with a rotary blow dryer.

Preferably, in the evaluation method consistent with the present invention, the desalting of the whole protein solution includes the following steps:

(1) redissolving the dried sample with 50 μl of solution B and uniformly mixing;

(2) activating a desalting column (Ziptip C18 column) with 10 μl of solution A, and repeating 5 times;

(3) then activating the desalting column (Ziptip C18 column) with 10 μl of solution B, and repeating 10 times;

(4) pipetting 10 μl of the sample in (1) into the activated column;

(5) rinsing the desalting column with 10 μl of solution B;

(6) performing sample eluting on the desalting column with 10 μl of solution A;

(7) quantifying the content of sample peptides using a Nanodrop spectrophotometer;

(8) adjusting the mass: ensuring the total protein in each centrifuge tube to be the same by selecting a total amount of protein, and according to the concentration, pipetting a certain amount of volume into a new centrifuge tube; and (9) performing blow-drying with a rotary blow dryer for later use;

where the solution A is a 60% acetonitrile solution containing 0.2% formic acid; and the solution B is ultrapure water containing 0.2% formic acid.

Preferably in the evaluation method consistent with the present invention, the LC-MS-MS analysis comprises of: the desalted and dried sample is redissolved with 10 μl of ultrapure water containing 0.2% formic acid, transferred to an inner tube, and loaded into a mass spectrometer; peptide products are separated by reversed phase liquid chromatography identified by tandem mass spectrometry with a nano-liter ion source using an LTQ-Orbitrap mass spectrometer, the specific steps are as follows: peptides are acidified with 0.1% formic acid, then a sample solution is injected into the system by an automatic sampler, then a loading buffer is pumped at a flow rate of 4 μl/min, and the sample is automatically loaded along with the loading buffer to the nanoliter liquid chromatograph mass spectrometer equipped with a nano-capturing column; after 8 min, the peptides are subjected to gradient elution and separation with 3%-55% of buffer B, the buffer flow rate is 300 nL/min, and the elution time is 112 min; the remaining peptides are further subjected to gradient elution with 55%-98% of buffer B, and the elution time is 5 min; the separated peptides are subjected to mass spectrometry scanning on LTQ OrbitrapXL, normalized collision energy of collision-induced dissociation is set to 35, resulting fragments are detected at a normal resolution in a linear ion trap, and a locking mass is set to 445.120020. The loading buffer is 2% acetonitrile, containing 0.1% formic acid in HPLC grade water; and the buffer B is 80% acetonitrile, containing 0.1% formic acid in HPLC grade water.

Preferably in the evaluation method consistent with the present invention, the searching parameters of the Max-Quant_1.5.8.3 software used in database searching are set to be:

| Item | Value |
|---|---|
| Main search ppm | 6 |
| Missed cleavage | 2 |
| MS/MS tolerance ppm | 20 |
| De-isotopic | True |
| Enzyme | Trypsin |
| Fixed modifications | Carbamidomethyl (C), |
| Variablemodifications | Oxidation (M), Acetyl (Protein N-term) |
| Decoy database pattern | reverse |
| Label free quantification (LFQ) | True |
| LFQ minratio count | 1 |
| Match between runs | 2 min |
| Peptide FDR | 0.01 |
| Protein FDR | 0.01 |

Preferably in the evaluation method consistent with the present invention, the dietary proteins include meat proteins, milk proteins and plant proteins; the meat proteins include proteins derived from beef, pork, mutton, fish, chicken and duck; the milk protein is casein; and the plant proteins include proteins derived from *glycine max*, hordeumvulgare, triticumaestivum, *Sorghum bicolor, Oryza sativa* and *Zea mays*.

Preferably in the evaluation method consistent with the present invention, the data processing further includes performing t-test between groups to obtain differential proteins, and then obtaining a biological process in which the differential proteins are involved by biological signal analysis.

Beneficial Effects

The innovation of the present invention is that proteomics techniques are used to identify proteins and digestive products thereof in different intestinal segments. On this basis, the sources (diet, host or intestinal microorganisms) of the proteins of the contents in different intestinal segments and the contents thereof can be judged. Through bioinformatics analysis, the function of differential proteins in the body can be further understood, where the gene expression of enzymes related to protein digestion and metabolism may be different, thereby providing a scientific basis for further scientific evaluation of protein digestion and utilization. The method can be extended for analyzing proteins and digestion products thereof in feces, and simplifying the evaluation procedure of the digestibility of proteins.

BRIEF DESCRIPTION OF THE DRAWINGS

FIGS. 2A-2C Functional analysis diagram of differential proteins in high-salt and low-salt diet groups FIG. 2A GO analysis of differential proteins, GO analysis including biological processes, cellular composition, and molecular function.

DETAILED DESCRIPTION

A method for evaluating in vivo protein nutrition based on an LC-MS-MS technique, includes the following steps:

Step 1: Collecting contents from different intestinal segments (duodenum, jejunum, cecum and colon). A certain amount of contents (W, mg) are taken into a 2 ml grinding tube (3-5 zirconium beads). RIPA lysate (strong) (1:100, W/V, Beyotime), a phosphatase inhibitor (1%, v/v, Sigma, P8340) and a protease inhibitor (1%, v/v, Sigma, P2850) are added. The contents are put into a Precellys homogenizer and oscillated (at 8500 rpm for 60 s, circulating for 3 times at intervals of 30 s), and put into a 4° C. pre-cooled centrifuge after being oscillated. Centrifugation is performed at 14000×g for 15 min, and the supernatant is taken. The supernatant is transferred to a new centrifuge tube and centrifuged again (at 3500 rpm for 5 min) to get the supernatant and the supernatant is placed at −80° C. for further use.

Step 2: Determining the concentration of proteins in contents of different intestinal segments by a BCA kit (Bio-Rad, USA).

Step 3: Treating before carrying out mass spectrometry (digesting and desalting of a whole protein solution):

Digesting of the Whole Protein Solution:

I. Reagents:
1. Denaturing buffer: 8M urea, 50mMTris-HCl (pH8.0)
2. 1M DTT (Dithiothreitol, Sigma, 646563-10 X.5 ML)
3. 0.5M IAM (Iodoacetamide, Sigma, I1149-5G)
4. 50mMNH$_4$HCO$_3$ (pH7.8) (Ammonium bicarbonate, Sigma, A6141-25G)
5. Trypsin (0.1 μg/μl, 200 μl buffer added to a glass bottle of enzyme) (Promega, V5111)
6. 10KD ultrafiltration tube II. Operation Steps:
1. activating the 10KD ultrafiltration tube with ultrapure water, i.e. adding 200 μl of ultrapure water, and performing centrifugation at 14000×g for 15 min (at room temperature);
2. taking 200 μg of protein, calculating a volume for 200 μg of protein as X ml, then supplementing Y ml of 8M urea and 50mMTris-HCl (pH 8.0) to a 200 μl system (i.e. X+Y=200 μl) into the ultrafiltration tube, and performing centrifugation at 14000×g for 15 min;
3. adding 200 μl of 8M urea and 50mMTris-HCl (pH 8.0), performing centrifugation at 14000×g for 15 min;
4. adding 200 μl of 8M urea and 50mMTris-HCl (pH 8.0), 5 μl of 1M DTT to the solution, heating at 60° C. for 60 min, cooling to room temperature, and performing centrifugation at 14000×g for 15 min;
5. adding 200 μl of 8M urea and 50mMTris-HCl (pH 8.0), adding 20 μl of 0.5M IAM, performing incubating at room temperature in the dark for 45 min, and performing centrifugation at 14000×g for 15 min;
6. adding 200 μl of 50 mM NH$_4$HCO$_3$ (pH 7.8), performing centrifugation at 14000×g for 15 min, and repeating once;
7. renewing an ultrafiltration tube bottom tube, adding 200 μl of 50 mM NH$_4$HCO$_3$ (pH 7.8), and according to the ratio of Trypsin to substrate protein at 1:50, adding an enzyme solution (i.e., adding 40 μl), and performing incubating at 37° C. for 16 hr (overnight);
8. performing centrifuging at 14000×g for 25 min, adding 50 μl of 50 mM NH$_4$HCO$_3$ (pH 7.8), performing centrifugation at 14000×g for 25 min, where the contents in the bottom tube are the peptides after enzymatic hydrolysis, and adding formic acid to the solution to a final concentration of 0.2%; and
9. transferring a sample into a 1.5 ml centrifuge tube and performing blow-drying with a rotary blow dryer.

Desalting of the Whole Protein Solution:

I. Reagents:
1. Solution A (60% ACN solution containing 0.2% FA)
2. Solution B (ultrapure water containing 0.2% FA)
3. Ziptip desalting column (10 μl) (Merck Millipore, ZTC18S096)

FA: Formic Acid, chromatographic grade
ACN: Acetonitrile, chromatographic grade

II. Operation Steps:
1. redissolving the dried sample with 50 μl of solution B and mixing;
2. activating the desalting column (Ziptip C18 column) with 10 μl of solution A, and repeating 5 times;
3. then activating the desalting column (Ziptip C18 column) with 10 μl of solution B, and repeating 10 times;
4. pipetting 10 μl of the sample in (1) into the activated column;
5. rinsing the desalting column with 10 μl of solution B;
6. performing sample elution on the desalting column with 10 μl of solution A;
7. quantifying sample peptides using a Nanodrop spectrophotometer;
8. adjusting the mass: ensuring the total protein in each centrifuge tube to be the same by selecting a total amount of protein, and according to the concentration, pipetting a certain amount of volume into a new centrifuge tube; and
9. performing blow-drying with a rotary blow dryer for later use.

III. Matters Need Attention
1. The desalting column is activated with the solution A first and then the solution B to ensure that the column is a water phase when the sample is loaded.
2. When loading, patience is needed because the concentration is too high, and the suction speed may be very slow.
3. Salt is eluted by a water phase, and protein is eluted by an organic phase.

Step 4 (LC-MS-MS):

The blow-dried sample is redissolved with 10 μl of solution B, transferred to an inner cannula after redissolving, and loaded into a mass spectrometer. Peptides are separated by carrying out reversed phase liquid chromatography using a nanoliter liquid chromatograph mass spectrometer (DIONEX Thermo Scientific), and identified by a nanoliter ion source by tandem mass spectrometry using an LTQ-Orbitrap mass spectrometer (Thermo Scientific). Peptide samples are acidified with 0.1% formic acid (FA), and sample solutions in loading buffer (2% acetonitrile, containing 0.1% formic acid in HPLC grade water) are automatically loaded to the nano liquid chromatograph mass spectrometer (Acclaim PepMap100C18, 75 μm×2 cm, 3 μm, 100 Å, Thermo Scientific) equipped with a nano-capturing column at a rate of 4 μl/min. After 8 min, the peptides are eluted and separated by passing a gradient of 3%-55% of the buffer B (80% acetonitrile, containing 0.1% formic acid in HPLC grade water) on an analytical column (AcclaimPepMapRSLC, C18, 75 μm×15 cm, 3 μm, 100 Å, ThermoScientific) at a flow rate of 300 nL/min for 112 min. The remaining peptides are further separated by a short gradient of 55% to 98% of the buffer B for 5 min. The separated peptides are analyzed in LTQ OrbitrapXL. Scanning is performed from high-resolution mass spectrometry, if the intensity exceeds at least 5000 counts, and if they have at least a double charge, then the ten strongest peptide ions are selected for fragment analysis in the linear ion trap. The normalized collision energy of collision-induced dissociation (CID) is set to 35, and the resulting fragments are detected at a normal resolution in the linear ion trap. A locking mass option is activated, and a background signal with a mass of 445.120020 is used as the locking mass. The ions of each selected fragment are excluded by dynamic exclusion for 60 seconds.

Step 5 (Database Searching):

MaxQuant_1.5.8.3 software (Max-Planck Institute of Biochemistry) is used to search for 30 individual original spectral files running on shotgun LC-MS/MS, respectively, where the searching parameters of the MaxQuant software are set to be:

| Item | Value |
| --- | --- |
| Main search ppm | 6 |
| Missed cleavage | 2 |
| MS/MS tolerance ppm | 20 |
| De-isotopic | True |
| Enzyme | Trypsin |
| Fixed modifications | Carbamidomethyl (C) |
| Variable modifications | Oxidation (M), Acetyl (Protein N-term) |
| Decoy database pattern | reverse |
| Label free quantification (LFQ) | True |
| LFQ min ratio count | 1 |
| Match between runs | 2 min |
| Peptide FDR | 0.01 |
| Protein FDR | 0.01 |

| Protein source | Application type |
| --- | --- |
| Dietary proteins | Meat proteins<br>Beef: *Bubalusbubalis*<br>Pork: *Susscrofa*<br>Mutton: *Ovisaries Capra hircus*<br>Fish: *Acipensergueldenstaedtii*<br>Chicken: *Gallus gallus*<br>Duck: *Anasplatyrhynchos*<br>Milk proteins<br>Casein: *Bostaurus*<br>Vegetable proteins<br>Soybean protein: *Glycine max*<br>Barley: *hordeumvulgare*<br>Wheat: *Triticumaestivum*<br>Sorghum: *Sorghum bicolor*<br>Rice: *Oryza sativa*<br>Corn: *Zea mays* |
| Host proteins (model animals) | Human: *Homo sapiens*<br>Mice: *Musmusculus*<br>Rat: *Rattusnorvegicus*<br>Xenopus: *Xenopuslaevis*<br>Drosophila: *Drosophila melanogaster*<br>Nematode: *Caenorhabditiselegans*<br>Zebrafish: *Daniorerio* |
| Microbial proteins | Self-built database (obtained from the Uniprot download collection, taking mice as an example)<br>*Acetobacterpasteurianus* IFO3283-32, *Alistipesshahii* WAL8301, *Akkermansiamuciniphila* ATCC BAA835, *Anaerococcusprevotii* DSM 20548, *AtopobiumParvulum*DSM 20469, *Bacillus cellulosilyticus* DSM 2522, *Bacillus cereus* ATCC 10987, *Bacillus licheniformis* DSM 13, *Bacillus subtilis* 168, *Bacteroidesfragilis* NCTC 9343, *Bacteroidesthetaiotaomicron* VPI5482, *Bacteroidesvulgatus* ATCC 8482, *Bacteroidesxylanisolvens* XB1A, *Bifidobacteriumadolescentis* ATCC 15703, *Bifidobacteriumanimalis* subsp. *lactis* DSM 10140, *Bifidobacteriumbifidum* S17, *Bifidobacteriumlongum* subsp. *infantis* ATCC 15697, Butyrate-producing *bacterium* SM4/1, Butyrate-producing *bacterium* SS3/4, *Anaerostipeshadrus*, *Butyrivibriofibrisolvens* 16/4, *Butyrivibrioproteoclasticus* B316, *Candida glabrata* CBS 138, *Clostridium acetobutylicum* ATCC 824, *Clostridium beijerinckii* NCIMB 8052, *Clostridium cellulolyticum* H10, *Clostridium cellulovorans* 743B, *Clostridium difficile* CD196, *Clostridium novyi* NT, *Clostridium perfringens* ATCC 13124, *Clostridium saccharolyticum* DSM 2544, *Coprococcuscatus* GD/7, *Desulfotomaculumreducens* MI-1, *Desulfovibriosalexigens* DSM 2638, *Eggerthellalenta* DSM 2243, *Enterobacter cloacae* ATCC 13047, *Enterococcus faecalis* V583, *Escherichia coli* K12, *Eubacteriumcylindroides* T2-87, *Eubacteriumeligens* ATCC 27750, *Eubacteriumlimosum* KIST612, *Eubacteriumrectale* ATCC 33656, *Faecalibacteriumprausnitzii* L2-6, *Finegoldia magna* ATCC 29328, *Fusobacteriumnucleatum* ATCC 25586, *Gordonibacterpamelaeae* 7-10-1-b, *Helicobacter pylori* 26695, *Klebsiella pneumonia* 342, *Lactobacillus acidophilus* NCFM, *Lactobacillus brevis* ATCC 367, *Lactobacillus casei* BL23, *L. delbrueckiibulgaricus* ATCC 11842, *Lactobacillus johnsonii* NCC 533, *Lactobacillus plantarum* WCFS1, *Lactobacillus reuteri* JCM 1112, *Lactococcuslactis* I11403, *Listeria monocytogenes* Clip80459, *Methanobrevibactersmithii* ATCC 35061, *Mycobacterium avium* 104, *Neisseria gonorrhoeae* NCCP 11945, *Parabacteroidesdistasonis* ATCC 8503, *Pediococcuspentosaceus* ATCC 25745, *Prevotellaruminicola* 23, *Propionibacterium acnes* SKI37, *Pseudomonasputida* KT2440, *Roseburiaintestinalis* M50/1, *Ruminococcusalbus* 7, *Ruminococcusbromii* L2-63, *Ruminococcusobeum* CAG:39, *Ruminococcus torques* L2-14, |

| Protein source | Application type |
|---|---|
| | *Saccharomyces cerevisiae* S288c, *Salmonella typhimurium* D23580, *Shigelladysenteriae* Sd197, *Slackiaheliotrinireducens* DSM 20476, *Staphylococcus aureus* NCTC 8325, *Staphylococcus epidermidis* ATCC 12228, *Streptococcus agalactiae* A909, *Streptococcus pneumoniae* TCH8431/19A, *Streptococcus thermophilus* LMG 311, *Streptomyces coelicolor*A3(2), *Yersinia enterocolitica* 8081. |

Step 6 (Data Processing):

Databases are searched in three aspects for proteins in the contents of the four intestinal segments, where the specific search sources are the protein databases of dietary proteins, host and intestinal microorganisms. By analyzing the protein data from three sources, the following information can be achieved: (i) the digestion of dietary proteins across the whole intestine, and the type and abundance of the identified proteins or peptides; (ii) the type and functions of proteins secreted by the host under the induction of the dietary proteins; and (iii) the composition of intestinal microorganisms responding to the dietary proteins and their crosstalk with the host. In addition, statistical analysis can be performed according to t-test between groups to obtain differential proteins, and then a biological process in which the differential proteins are involved is obtained by biological signal analysis.

Embodiment 1

Figure 1:
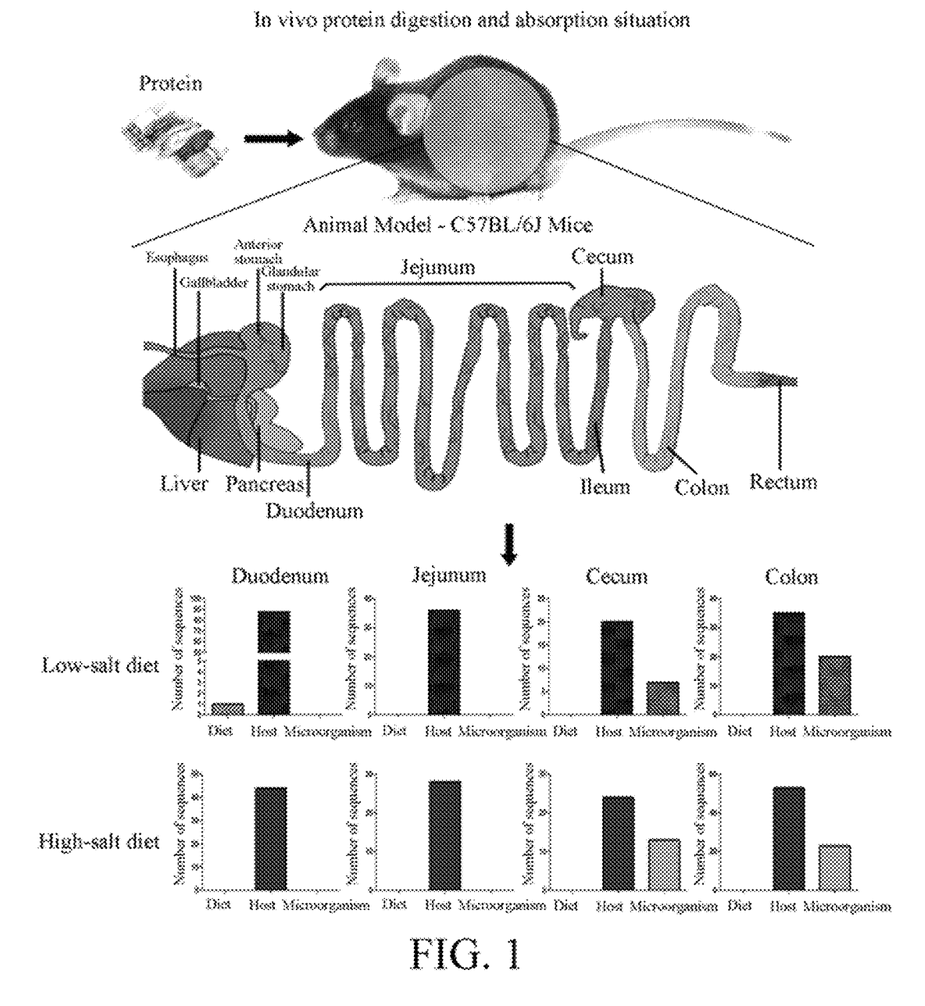
FIG. 1 In vivo protein digestion and absorptionsituation

C57BL/6J mice were used as animal models, the mice were fed with low salt (0.25%) and high salt (3.5%) diets, with 5 mice in each group, and the experimental period was 8 weeks. After the completion of the experiment, the mice were sacrificed by cervical dislocation, and the contents of the duodenum, jejunum, cecum and colon were collected and placed in a 2 ml plastic tube, quickly frozen in liquid nitrogen, and transferred to −80° C. for lateruse. With ten mice, and the contents of four kinds of intestinal segments, there were totally 40 samples. Protein extraction was performed by addition of RIPA lysate, a phosphatase inhibitor and a protease inhibitor (method as above). After extracting the proteins, the concentration was determined by a BCA kit, and the mass was adjusted by digesting and desalting according to the operation steps. The total protein in each centrifuge tube selected in this experiment was 1.5 μg. After LC-MS-MS and database searching, the protein identification results of three sources of four intestinal segments were obtained (FIG. 1).

In terms of dietary protein sources, a total of 452 proteomes were identified from all intestinal contents by searching the Bostaurus (casein) database. After filtering by repeatability and matching, the sequence of the tested peptides can be matched to 54 proteins. Most of the proteins are casein kinases and other enzymes. Only a small amount of β-lactoglobulin (fragment) can be detected in the LSD group as a component of casein. There is no statistical significance in the difference in the composition of dietary-based protein fragments between the two groups. Therefore, it can be observed that casein is a protein with better digestion and absorption properties, and is easily digested by pepsin, trypsin and chymotrypsin in the small intestine and then absorbed by the intestinal segments. Therefore, through the identification of mass spectrometry, the digestion process of proteins in the body can be clearly understood.

Figure 2A:
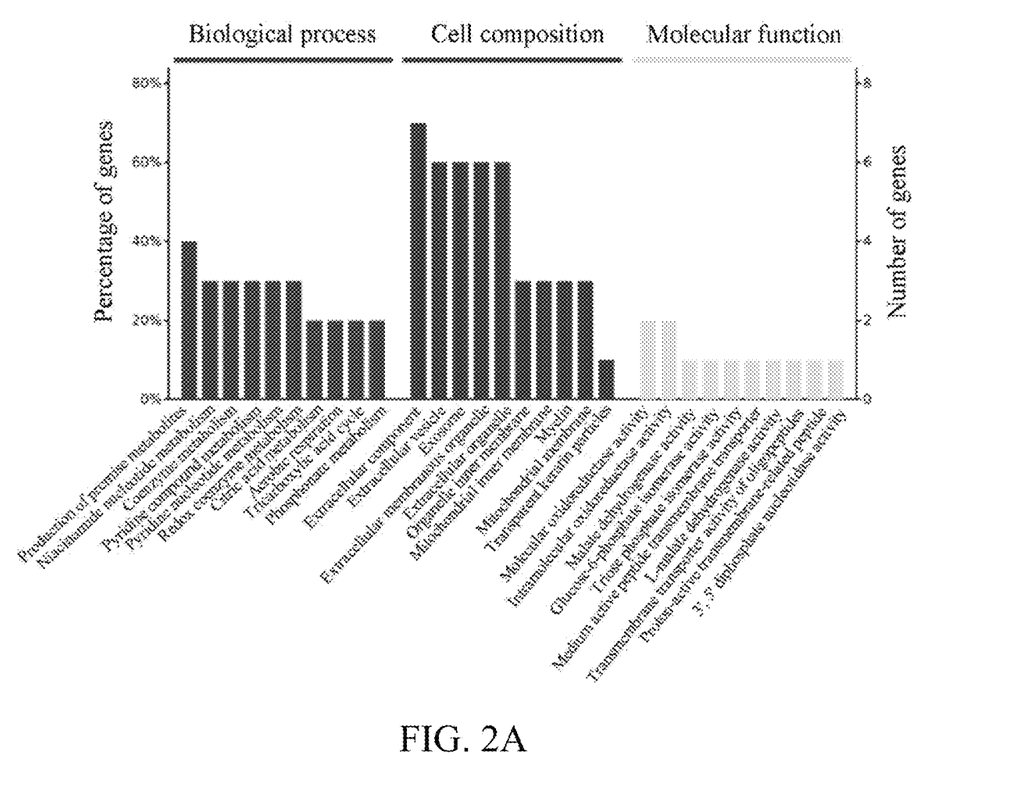
Figure 2B:
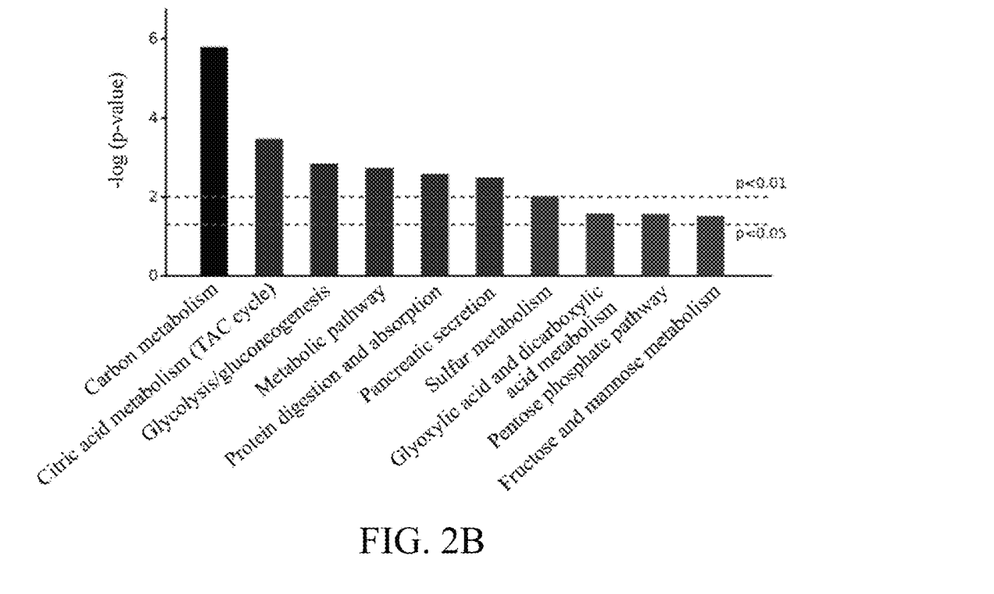
FIG. 2B KEGG analysis of differential proteins, mainly including the metabolic pathway analysis of functional genes involved.
Figure 2C:
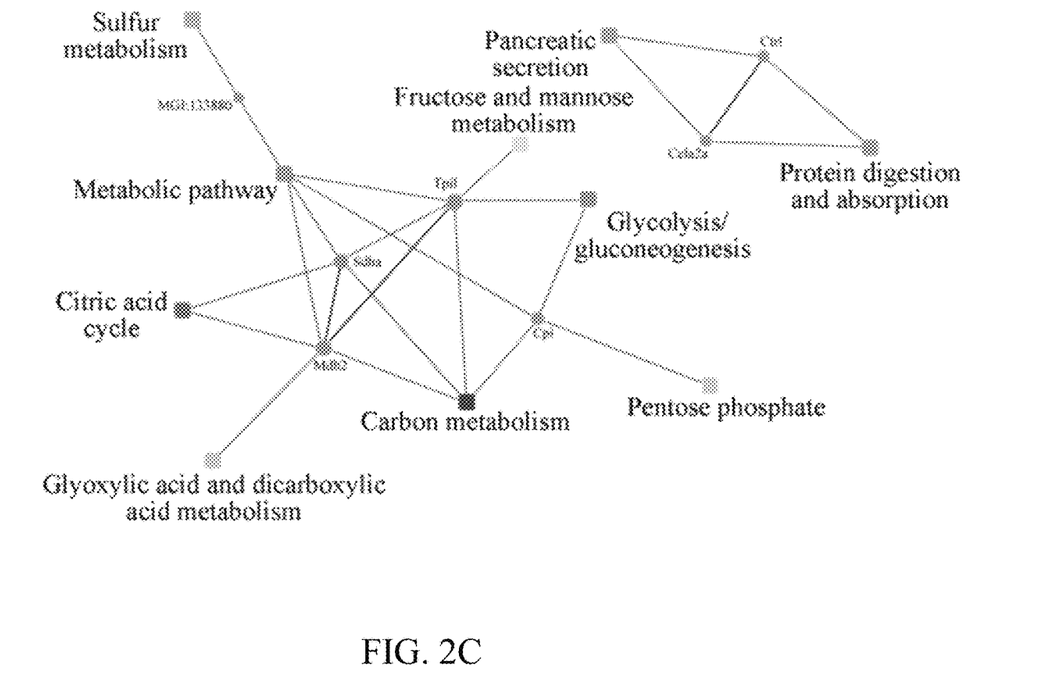
FIG. 2C Differential protein interaction analysis (PPI).

In terms of host protein sources, 179 and 149 unique peptide sequences were identified from the four intestinal contents of the low-salt diet group and the high-salt diet group by searching the Musmusculus(mice) database. There were 20 different proteins in the two duodenum groups, and low abundance is expressed in the high-salt diet group. The number of host-based peptides decreases from the duodenum to the cecum, and increases from the cecum to the colon. Some of the 20 differential proteins are digestive enzymes, including chymotrypsin B, pancreatic triacylglycerol lipase precursor, carboxypeptidase A1 precursor, and carboxypeptidase B1. These results suggest that a high-salt diet may inhibit the secretion of digestive enzymes, resulting in a low level of protein digestion in the high-salt diet group. In addition to digestive enzymes, several cytoplasmic components were identified, including α-actin, tropomyosinα-1 chain, cadherin 17, and vesicle protein VAT-1 homologue, where the cadherin 17 was involved in calcium ion binding, the vesicle protein VAT-1 homologue was related to oxidoreductase activity, and the phosphoglyceratemutase 1 was involved in glycolysis process. Bioinformatics tools in the OimcsBean Omics Analysis System (http://www.omicsbean.com:88/) were used to analyze data of differential protein to obtain more information about the pathways involved. Bioinformatics analysis mainly includes three aspects, i.e. GO (Gene Ontology) analysis, KEGG (Kyoto Encyclopedia of Genes and Genomes) analysis and PPI (protein-protein interaction) analysis. In the GO analysis results, most of the identified proteins were identified to be involved in the metabolic process, particularly in the metabolism of pyridine and coenzymes. The proteins were also one of the organelles and extracellular components. In terms of molecular function, most proteins were involved in enzymatic activities, including oxidoreductase, malate dehydrogenase, glucose-6-phosphate isomerase and triose phosphate isomerase (FIG. 2A). In the KEGG analysis results, the active pathways were involved in secretion and metabolism, including protein digestion, absorption, and pancreatic secretion (FIG. 2B). The results indicated that a high-salt diet may have an inhibitory effect on pancreatic secretion by inhibiting the secretion of trypsin. To further explore more relevant information for identifying proteins, more comprehensive bioinformatics analysis of protein data was performed to integrate protein-protein interaction networks. Seven proteins are considered to be key nodes in the biological interaction network (FIG. 2C). A chymotrypsin-like elastase family member 2A precursor (P05208) and papamycin (Q9E205) are highly correlated with pancreatic secretion and protein digestion and absorption. Proteins encoded by Sdha and Tpi1 are involved in a number of metabolic processes, including a succinic acid metabolism process, gluconeogenesis and a pentose phosphate branching process (FIG. 2C).

In terms of microbial protein sources, by searching the Bacteria (self-built) database, the relevant database creation is obtained based on literature from a Uniprot download collection. A total of 63 peptides were clearly identified and quantified, but the corresponding 18 proteins were not annotated. The proteins are secreted by the intestinal microorganisms that metabolize saccharides and proteins. In the colon contents, 17 microbial proteins are common between the two groups, where five proteins were highly expressed in the low-salt diet group compared with the high-salt diet group. These proteins included cytidine kinase, triggering factors, 6-phosphogluconate dehydrogenase, transporters, and undecaprenyl-diphosphatase. These proteins are secreted by Atopobiumparvulum, *Lactobacillus acidophilus, Lactobacillus brevis*, anorexia, and *Streptococcus agalactiae*, respectively. Cytidine kinase is involved in pyrimidine metabolism, ATP binding, transferase, and cytidylate kinase activity. The triggering factor are associated with protein transport, which acts as a molecular chaperone by maintaining newly synthesized secreted and non-secreted proteins. In addition, the triggering factors are involved in cell cycle, cell division, protein folding, and peptidyl-prolylcis-trans isomerase activity, thereby modulating the activity. The 6-phosphogluconate dehydrogenase is involved in the pentose phosphate pathway. The transporters are proteins that ensure the function of transferring materials in living organisms and play an important role in the transport of sodium molecules. Therefore, high concentrations of sodium may result in high expression of transporters. Undecaprenyl-diphosphatase is involved in dephosphorylation, peptidoglycan biosynthesis and regulation of cell shape. Two other proteins (acetyl glutamate kinase and PBSX phage manganese-containing catalase) have a relatively high abundance in the low-salt diet group and are secreted by *Clostridium* and *Bacillus subtilis* BEST7613. The acetyl glutamate kinase is involved in arginine and proline biosynthesis and ATP binding, and catalyzes ATP-dependent phosphorylation of N-acetyl-L-glutamate. PBSX phage manganese-containing catalase is produced by *Bacillus subtilis*. When the cells are in an anaerobic environment, the intracellular catalase activity decreases. While under aerobic conditions, removal of thiosulfate from or addition of manganese to a culture medium tends to increase the catalase activity.

What is claimed is:
1. A method for determining in vivo protein nutrition based on an LC-MS-MS technique, comprising of the following steps:
  (1) collecting samples such that each sample comprises contents from a different intestinal segment relative to another sample, and extracting and isolating protein ingredients from each sample;
  (2) determining the concentration of proteins in each sample;
  (3) treating each sample before carrying out mass spectrometry by performing digestion, desalting, and blow-drying of a whole protein solution of each sample;
  (4) performing LC-MS-MS analysis of a peptide product that is obtained by carrying out reversed phase liquid chromatography using a nanoliquid chromatograph mass spectrometer on the digested, desalted and blow-dried samples, then performing an analysis by a nano-liter ion source by tandem mass spectrometry using an LTQ-Orbitrap mass spectrometer, the analysis comprising the following steps:
    a desalted and blow-dried sample is redissolved with 10 μl of ultrapure water containing 0.2% formic acid, transferred to an inner tube, and loaded into a mass spectrometer;
    peptide products are separated by reversed phase liquid chromatography and identified by tandem mass spectrometry with a nanoliter ion source using an LTQ-Orbitrap mass spectrometer, with specific steps as follows:
      peptides are acidified with 0.1% formic acid, then a sample solution is injected into the system by an automatic sampler, then a loading buffer is pumped at a flow rate of 4 μl/min, and the sample is automatically loaded along with the loading buffer to the nanoliter liquid chromatograph mass spectrometer equipped with a nano-capturing column;
      after 8 min, the peptides are subjected to gradient elution and separation with 3%-55% of buffer B, the buffer flow rate is 300 nL/min, and the elution time is 112 min;
      the remaining peptides are further subjected to gradient elution with 55%-98% of buffer B, and the elution time is 5 min;
      the separated peptides are subjected to mass spectrometry scanning on LTQ OrbitrapXL, normalized collision energy of collision-induced dissociation is set to 35, resulting fragments are detected at a normal resolution in a linear ion trap, and a locking mass is set to 445.120020,
      wherein the loading buffer is 2% acetonitrile, containing 0.1% formic acid in HPLC grade water; and the buffer B is 80% acetonitrile, containing 0.1% formic acid in HPLC grade water;
  (5) performing database searching using MaxQuant 1.5.8.3 software to search for 30 individual original spectral files running on a shotgun LC-MS/MS, respectively;
  (6) performing data processing by searching databases from three aspects for proteins in the contents of each intestinal segment sample, wherein the specific search sources are the protein databases of dietary proteins, host, and intestinal microorganisms, such that by analyzing the protein data from the three sources, the following information can be obtained:
    (i) the digestion of dietary proteins across the whole intestine, and the type and abundance of the identified proteins or peptides;
    (ii) the type and functions of proteins secreted by the host under the induction of the dietary proteins; and
    (iii) the composition of intestinal microorganisms responding to the dietary proteins and their crosstalk with the host.

2. The method according to claim 1, wherein the different intestinal segments are selected from the group consisting of duodenum, jejunum, cecum and colon.

3. The method according to claim 1, wherein the concentration of proteins in each sample in step (2) is quantified using a BCA kit.

4. The method according to claim 1, wherein the digestion of the whole protein solution in step (3) comprises of the following steps:
  (1) activating a 10KD ultrafiltration tube with ultrapure water;
  (2) taking 200 μg of protein, calculating a volume for taking 200 μg of protein as X ml, then supplementing Y ml of 8M urea and 50mM_Tris-HCl (pH 8.0) to a 200 μl system (i.e. X+Y=200μl) into the ultrafiltration tube, and performing centrifugation at 14000×g for 15 min;

(3) adding 200 µl of 8M urea and 50mM_Tris-HCl (pH 8.0), and performing centrifugation at 14000×g for 15 min;
(4) adding 200 µl of 8M urea and 50mM_Tris-HCl (pH 8.0), 5 µl of 1 M DTT to the dissolved pellet in step (3), heating at 60° C. for 60 min, cooling to room temperature, and performing centrifugation at 14000×g for 15 min;
(5) adding 200 µl of 8M urea and 50mM_Tris-HCl (pH 8.0), 20 µl of 0.5 M IAM to the dissolved pellet in step (4), incubating at room temperature in the dark for 45 min, and performing centrifugation at 14000×g for 15 min;
(6) adding 200 µl of 50 mM $NH_4HCO_3$ (pH 7.8) to the dissolved pellet in step (5), performing centrifugation at 14000×g for 15 min, and repeating once;
(7) using a new ultrafiltration tube bottom tube, adding 200 µl of 50 mM $NH_4HCO_3$ (pH 7.8), and according to the ratio of Trypsin to substrate protein at 1:50, adding 40 µl of enzyme solution, and incubating at 37° C. for 14-18 h;
(8) after incubation, performing centrifugation at 14000×g for 25 min, supplementing 50 µl of 50 mM $NH_4HCO_3$ (pH 7.8) to the pellet, performing centrifugation at 14000×g for 25 min, wherein the contents in the bottom tube are the peptides after enzymatic hydrolysis, and adding formic acid to the solution to a final concentration of 0.2%; and
(9) transferring a sample into a 1.5 ml centrifuge tube and performing blow-drying with a rotary blow dryer.

5. The method according to claim 1, wherein the desalting of the whole protein solution in step (3) comprises of the following steps:
(1) redissolving the dried sample with 50 µl of solution B and uniformly mixing;
(2) activating a desalting column (Ziptip C18 column) with 10 µl of solution A, and repeating 5 times;
(3) then activating the desalting column (Ziptip C18 column) with 10 µl of solution B, and repeating 10 times;
(4) pipetting 10 µl of the sample in (1) into the activated column;
(5) rinsing the desalting column with 10 µl of solution B;
(6) eluting sample on the desalting column with 10 µl of solution A;
(7) quantifying the content of sample peptides using a Nanodrop spectrophotometer;
(8) adjusting the mass: ensuring the total protein in each centrifuge tube to be the same, and according to the concentration, pipetting a certain amount of volume into a new centrifuge tube; and
(9) performing blow-drying with a rotary blow dryer for subsequent use;
wherein the solution A is a 60% acetonitrile solution containing 0.2% formic acid; and the solution B is ultrapure water containing 0.2% formic acid.

6. The method according to claim 1, wherein the searching parameters of the MaxQuant 1.5.8.3 software used in database searching are set to be:

| Item | Value |
| --- | --- |
| Main search ppm | 6 |
| Missed cleavage | 2 |
| MS/MS tolerance ppm | 20 |
| De-isotopic | True |
| Enzyme | Trypsin |
| Fixed modifications | Carbamidomethyl (C) |
| Variable modifications | Oxidation, Acetyl |
| Decoy database pattern | reverse |
| Label free quantification (LFQ) | True |
| LFQ min ratio count | 1 |
| Match between runs | 2 min |
| Peptide FDR | 0.01 |
| Protein FDR | 0.01 |

7. The method according to claim 1, wherein the dietary proteins comprise of meat proteins, milk protein, and plant proteins;
wherein the meat proteins comprise proteins are derived from beef, pork, mutton, fish, chicken, and duck;
wherein the milk protein is casein; and
wherein the plant proteins comprise of proteins derived from soybean, barley, wheat, sorghum, rice, and corn.

8. The method according to claim 1, wherein the data processing further comprises of performing a t-test between groups of samples which were subjected to different diets in order to obtain differential proteins, and then obtaining biological processes in which the differential proteins are involved.

* * * * *